United States Patent [19]

Jewett et al.

[11] Patent Number: 5,544,647
[45] Date of Patent: Aug. 13, 1996

[54] METERED DOSE INHALATOR

[75] Inventors: Warren Jewett; Frederick A. Ebeling, both of Cary, N.C.

[73] Assignee: IEP Group, Inc., Raleigh, N.C.

[21] Appl. No.: 346,524

[22] Filed: Nov. 29, 1994

[51] Int. Cl.⁶ ........................................... A61M 11/00
[52] U.S. Cl. ........................ 128/200.23; 128/203.12
[58] Field of Search ................ 128/200.14, 200.23, 128/202.22, 202.21, 203.12, 203.15, 203.23

[56]  References Cited

U.S. PATENT DOCUMENTS

| | | | |
|---|---|---|---|
| 4,300,548 | 11/1981 | Jones | 128/204.21 |
| 4,534,345 | 8/1985 | Wetterlin | 128/203.15 |
| 4,677,975 | 7/1987 | Edgar et al. | 128/200.14 |
| 4,947,875 | 8/1990 | Brooks et al. | 131/330 |
| 4,955,371 | 9/1990 | Zamba et al. | 128/200.18 |
| 5,020,527 | 6/1991 | Dessertine | 128/200.23 |
| 5,224,474 | 6/1993 | Bloomfield | 128/201.19 |
| 5,227,764 | 7/1993 | Umemoto | 340/552 |
| 5,284,133 | 2/1994 | Burns et al. | 128/200.23 |
| 5,363,842 | 11/1994 | Mishelevich et al. | 128/200.14 |
| 5,392,768 | 2/1995 | Johansson et al. | 128/200.14 |
| 5,394,866 | 3/1995 | Ritson et al. | 128/200.14 |

FOREIGN PATENT DOCUMENTS

| | | | |
|---|---|---|---|
| 87/04354 | 7/1987 | WIPO | 128/200.23 |
| 90/10470 | 9/1990 | WIPO | 128/203.15 |
| 91/06334 | 5/1991 | WIPO | 128/200.23 |
| 92/17231 | 10/1992 | WIPO | 128/200.23 |

*Primary Examiner*—Edgar S. Burr
*Assistant Examiner*—Eric P. Raciti
*Attorney, Agent, or Firm*—Kane, Dalsimer, Sullivan, Kurucz, Levy, Eisele and Richard

[57] ABSTRACT

A metered dose inhaler is described having an improved electronic counting means to indicate the doses remaining in the aerosol canister component of the inhaler assembly.

10 Claims, 8 Drawing Sheets

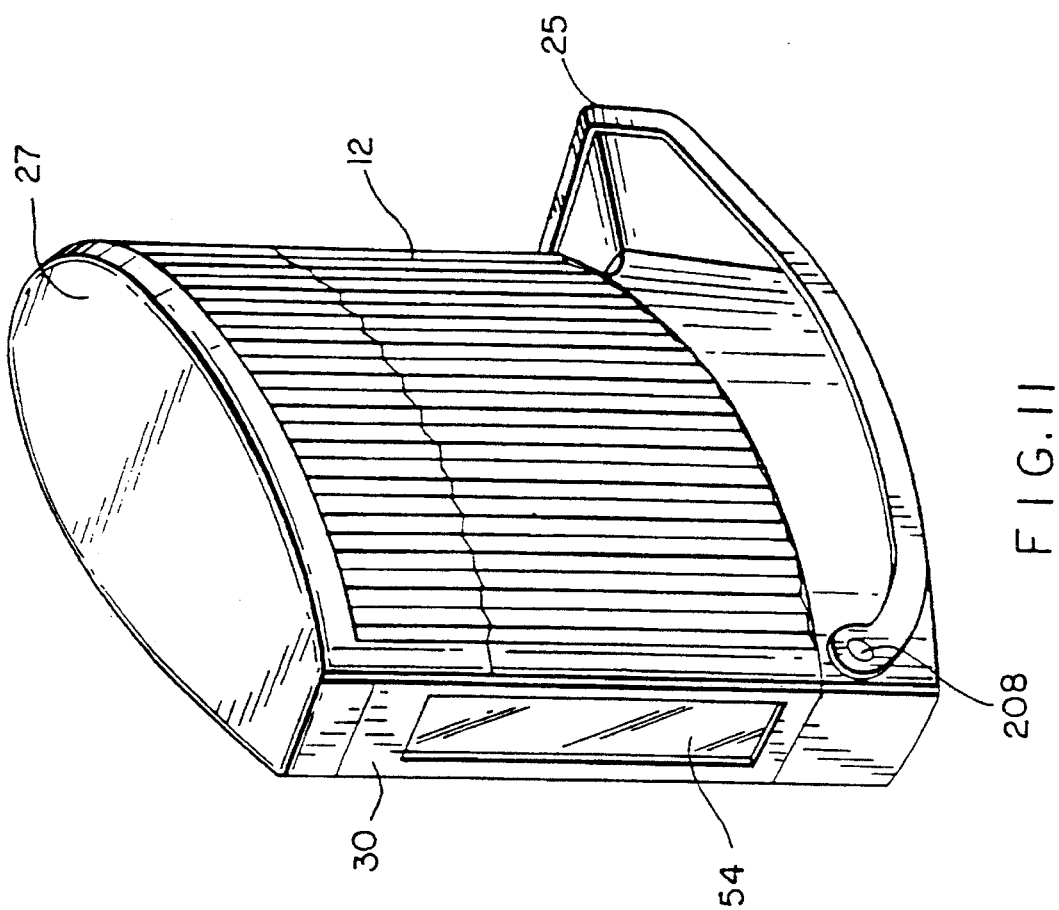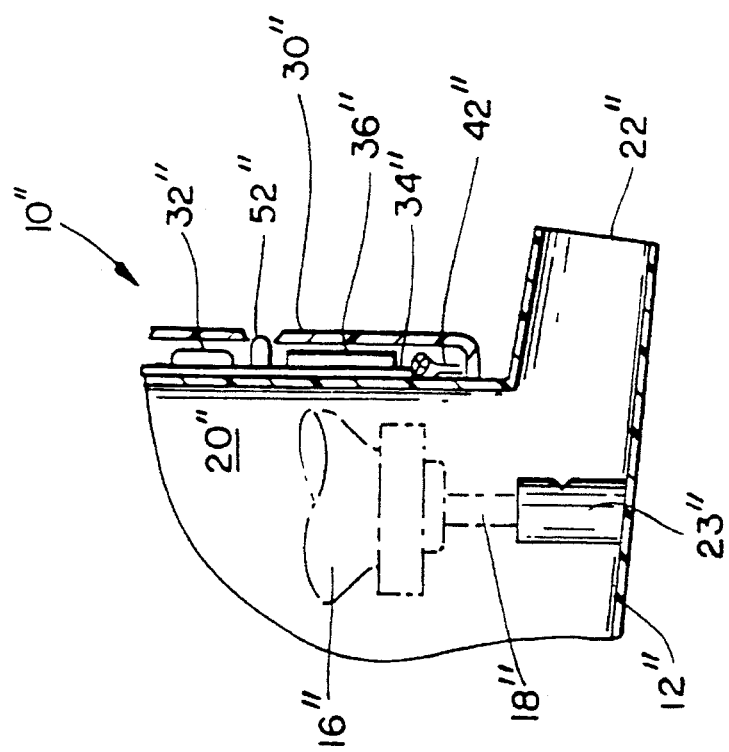

METERED DOSE INHALATOR

BACKGROUND OF THE INVENTION

1. Field of Invention

This invention is directed to inhalers for the controlled inhalation of medication by a patient through self-activation. More particularly, it is directed to an inhaler which releases measured doses of pressurized medication, in spray form into the mouth or nose, and constantly accounts for the doses remaining.

2. Brief Description of Related Art

The use of inhalers is well known and the art has developed over the past twenty five years to cover many versions of the basic concept of a "pumping" type medication applicator. The device may be manually pumped (such as described in U.S. Pat. No. 5,284,132) or a pumping like cycle may be utilized. The medication may be repeatedly released from a disposable canister to create repeated sprays or inhalations as needed.

Representative of the early inhalers for oral and intranasal administration of medications are those described in, for example, U.S. Pat. Nos. 3,361,306; 3,183,907; 3,565,070; 4,206,758; 4,803,978; 4,934,358; 4,955,371; 5,060,643; and 5,351,683. Representative of nasal-pharyngeal inhalers for large mammals such as a horse is that described in U.S. Pat. No. 5,062,423.

Metered dose inhalers (MDIs) are, at present, the most efficient and best-accepted means for accurately delivering drugs in small doses to the respiratory tract. Therapeutic agents commonly delivered by the inhalation route include bronchodilators ($B_2$ agonists and anticholinergics), corticosteroids, and anti-allergics. Inhalation may also be a viable route for anti-infective, vaccinating, systemically acting and diagnostic agents, as well as anti-leukotrienes, antiproteases and the like.

MDIs are available in several types. Most frequently, MDIs comprise a pressure resistant container (canister) typically filled with a product such as a drug dissolved in a liquified propellant, or micronized particles suspended in a liquified propellant. The container is fitted with a metering valve. The valve is movable from an inner (charging) position to an outer (discharging) position. A spring bias holds the valve in the charging position until forced to the discharging position. Actuation of the metering valve allows a metered portion of the container content to be released, whereby the pressure of the liquified propellant carries the dissolved or micronized drug particles out of the container and to the patient. A valve actuator also functions to direct the aerosol as a spray into the patient's oropharynx. Surfactants are usually dissolved in the aerosol formulation and can serve the dual functions of lubricating the valve and reducing aggregation of micronized particles.

Representative of pharmaceutical formulations for use in metered dose inhalers are those described in U.S. Pat. No. 5,190,029. The MDI devices for administering such pharmaceutical formulations are also well known as seen for example in the descriptions given in U.S. Pat. Nos. 3,361,306; 3,565,070; and 4,955,371.

A disadvantage arising from use of the known devices is that the patient cannot determine the amount of medicament in the aerosol container at any given time. The containers are generally not transparent to view, being light protective of the contents. Shaking them will not always reveal auditory information as to their contents. In an extreme case this could mean that the patient, possibly suffering from severe bronchospasm or like emergency condition and needing a dose of medicament, will find that the aerosol container will not dispense a dose, because its contents have been previously exhausted. The problem has been recognized and consideration given to solutions. For example, U.S. Pat. No. 4,817,822 describes an inhaler device which includes a counting means for indicating the relative emptiness of a container or the number of doses dispensed. However, this inhaler counting mechanism is physically attached to the aerosol container as well as the inhaler, such as by a retaining ring or retaining cap. In one embodiment, the counting means is a separate sleeve fitting on the up-turned bottom of the aerosol container. It is easy to lose, not being integrated with the inhaler, but an ancillary unit slipped over the loose aerosol container. In another embodiment, the counting means requires a secured attachment to the aerosol container neck, which prevents removal of the container from the inhaler, even when empty. The inhaler device is only useful for use with the original aerosol container and can not be used with aerosol refill containers.

The U.S. Pat. No. 5,020,527 presents an improvement over the dose counting means of U.S. Pat. No. 4,817,822 wherein the mechanical counter can be replaced with an electronic counter. The improved inhaler can indicate the number of doses remaining in the aerosol container. However, the device is not fool-proof in operation, which can be a disadvantage in the hands of a severely debilitated, confused or forgetful patient. In households which include small children they have been known to "play" with the MDI's when unsupervised access is possible. Infants can accidentally reset or interfere with established counts in the mechanical devices. For example, the counter can be accidentally reset, obviating its usefulness and, in fact, misleading of the patient as to the true number of doses remaining in the container. Also, the counter can not be automatically reset when a full, new aerosol container (refill) is to be used. This can affect the accuracy of the count carried out.

In addition, the inhaler of the U.S. Pat. No. 5,020,527 still employs a mechanical trigger to actuate the counting means. It is subject to triggering of the counter without actual administration of a dose from the container, for example, when the aerosol container is removed and the inhaler device washed and disinfected, independent of the aerosol container.

These, and other problems associated with the inhalers of the prior art are solved by the present invention, described hereinafter.

SUMMARY OF THE INVENTION

The invention comprises apparatus for assembly with a canister containing a predetermined number of doses of a pharmaceutical formulation, for administration orally or intra-nasally, which comprises;

(a) a hollow, tube having
 (i) a first end adapted by size and configuration to hold the formulation;
 (ii) a second open end adapted by size and configuration to couple with an oral or nasal orifice of a mammal;

(b) a formulation-directing element fixedly located within said tube hollow, and having continuous communication with the first end and the second open end, for directing the formulation through a portion of the hollow and out of the second open end of said tube, when the inhaler is activated by a user; and (c) microelectronic means associated with the tube for indicating the number of formulation doses remaining in the tube, after each activation;
said microelectronic means being activated by switch means isolated from exposure to the tube hollow.

The apparatus of the invention is useful to administer medications orally or intra-nasally to a mammal, including a human. It is relatively simple to operate, even by young children (6 to 12 years of age) who may require such treatment as the inhalers will provide.

The invention enables one to maintain a count of doses remaining for administration in MDIs of the type activated manually or by the act of inhalation, administering powders as well as liquid aerosols.

BRIEF DESCRIPTION OF THE DRAWINGS

Embodiments of the present invention will now be described with reference to the accompanying drawings in which:

FIG. 10 is a cross-sectional side view of a portion of another embodiment inhaler of the invention.

FIG. 11 is a view-in-perspective of another embodiment inhaler of the invention.

DETAILED DESCRIPTION OF THE PREFERRED EMBODIMENTS OF THE INVENTION

There are several embodiments of the invention, differing from each other in respect to the mode of actuating the microelectronic means.

Those skilled in the art will gain an understanding of the invention from a reading of the following description of the preferred embodiments when read in conjunction with a viewing of the accompanying drawings of FIGS. 1–14, inclusive.

EMBODIMENT A

Figure 1:
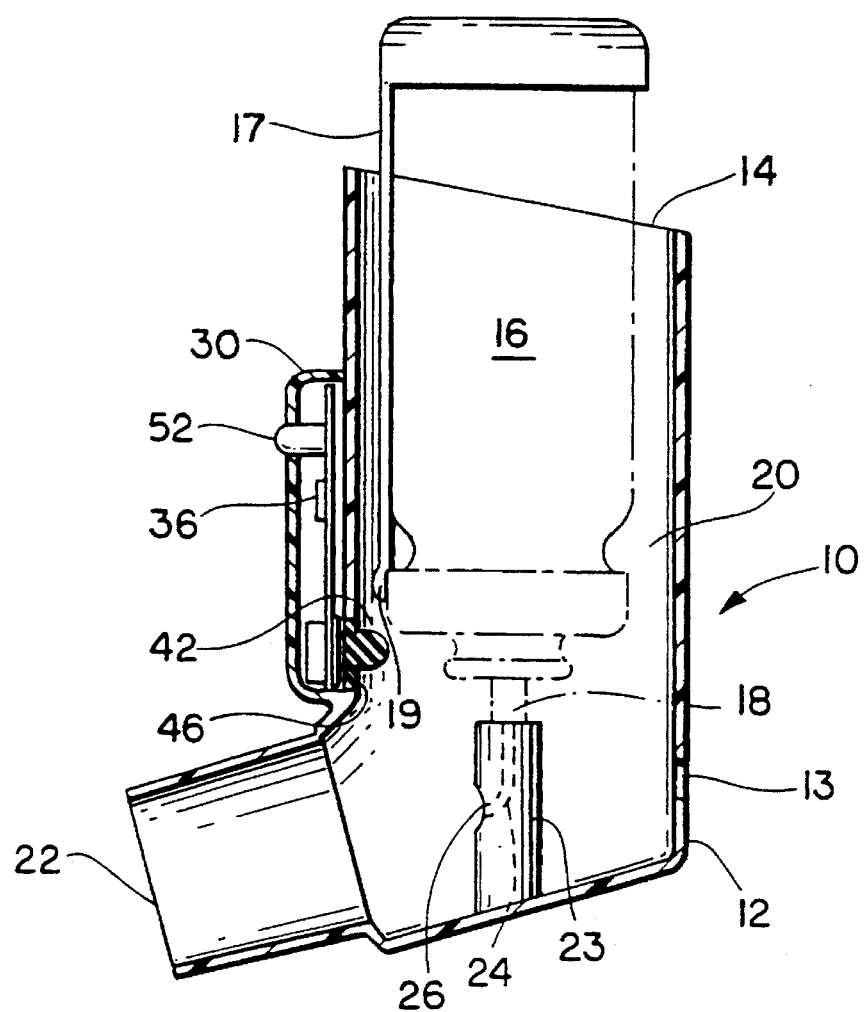
FIG. 1 is a cross-sectional in-part side view of an embodiment metered dose inhaler of the invention shown in assembly with a metered dose inhaler aerosol canister, shown prior to activation.
Figure 2:
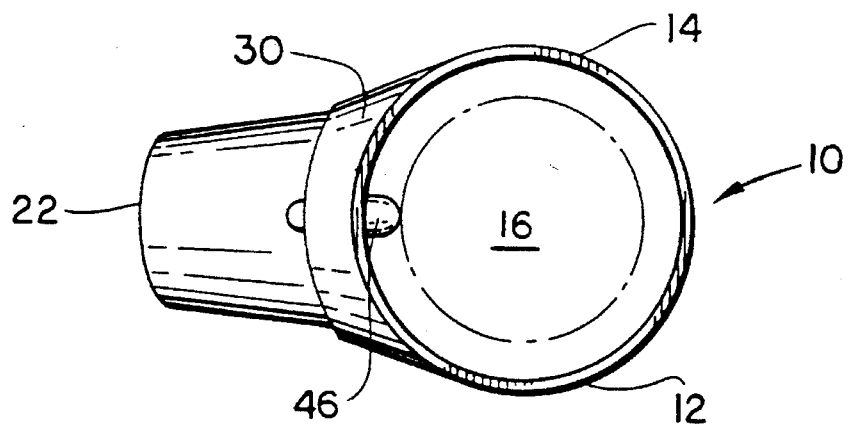
FIG. 2 is a top view of the assembly shown in FIG. 1.
Figure 4:
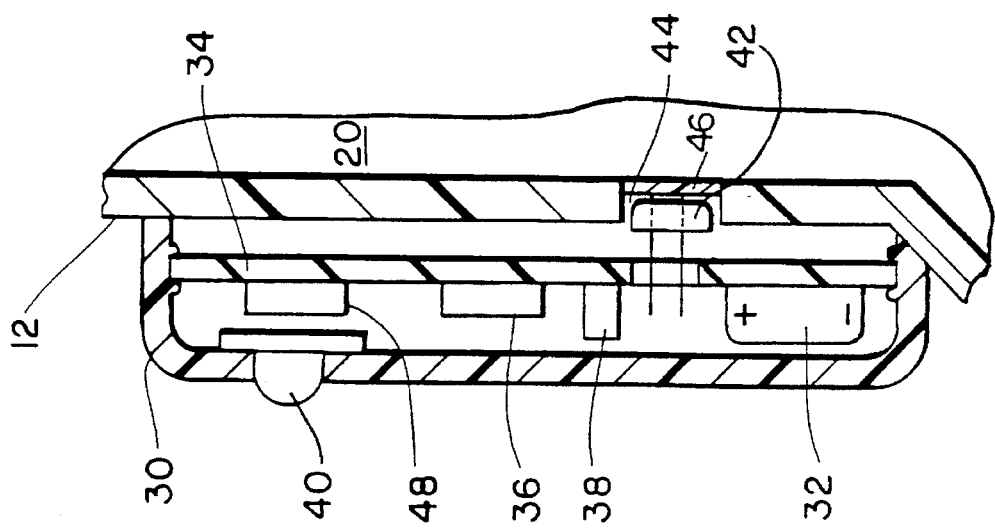
FIG. 4 is an enlarged view of the microelectronic means for indicating the number of doses remaining in the aerosol canister, in cross-section.
Figure 3:
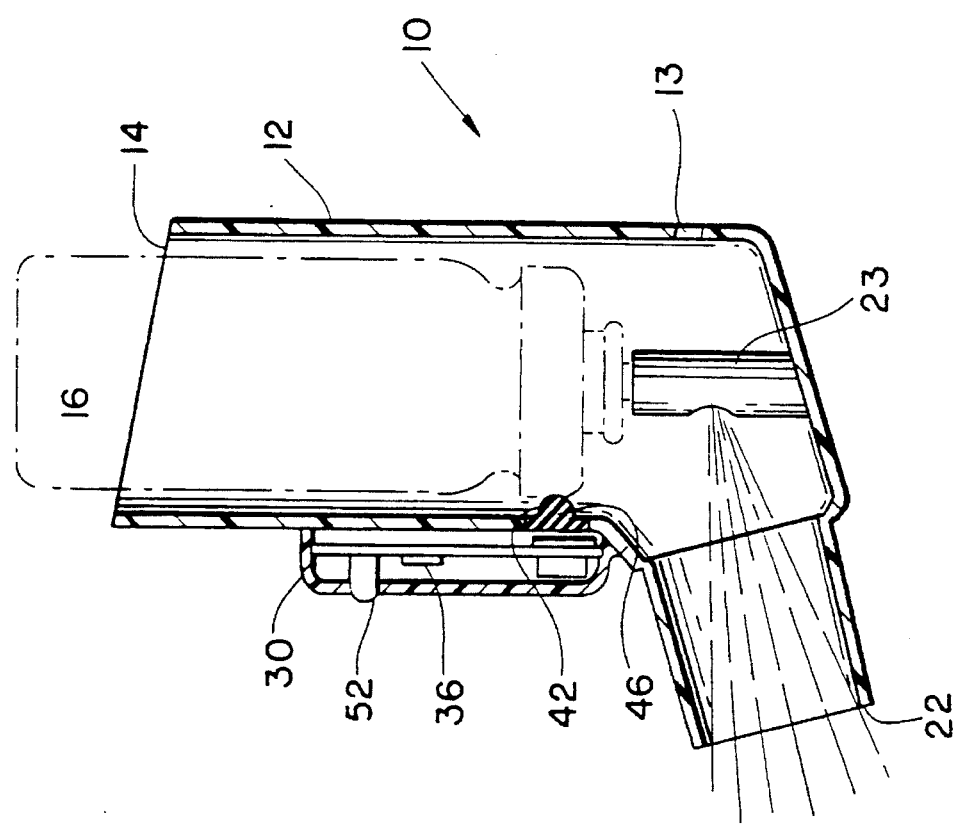
FIG. 3 is a view of the assembly shown in FIG. 1, during activation.
Figure 6:
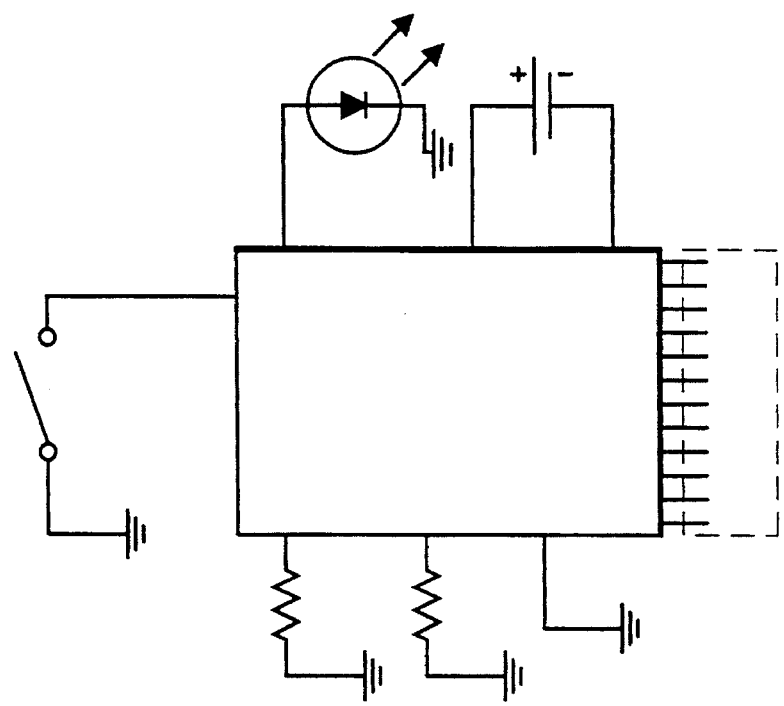
FIG. 6 is an illustration of an embodiment microelectronic circuit component of the microelectronic indicator means shown in FIGS. 4 and 5.

Referring first to FIG. 1, there is seen a cross-sectional side elevation of an embodiment metered dose inhaler 10 of the invention. The inhaler 10 is essentially a hollow tube 12 having a first open end 14, which by size and configuration is adapted to receive in assembly an aerosol canister 16. A small vent aperture 13 may be advantageous to vent the tube 12 during use, allowing ambient air in. The aerosol canister 16 is fitted with a conventional metering valve (not seen in FIG. 1) and spray stem 18. Such canisters 16 are commercially available from the Bespak Co., North Carolina, U.S.A. They may contain any of the pharmaceutical preparations conventionally used in oral and nasal medicators, such as described for example in the U.S. Pat. No. 5,190,029. The assembled tube 12 and canister 16 locates the canister 16 partially within tube 12 hollow 20, although other embodiments as described below may fully contain the canister 16. Open end 22 communicates with hollow 20 and is adapted by size and configuration to form a mouthpiece for insertion in the oral cavity of a patient and to couple or sealingly engage with the oral lips for inspiration and expiration of the breath of a mammal. Alternatively, end 22 can be adapted to engage with the patient's nasal passages. Within the hollow 20 is fixedly mounted a spray-directing element 23 which includes a continuous internal conduit 24. The conduit 24 couples with the stem 18 of the aerosol canister 16 and directs a metered dose therefrom out of nozzle 26 as a spray toward the open end 22 of the tube 12 when the canister 16 is pushed downwardly by the user. The valve of canister 16 is activated to release a metered dose. The valve is activated when the patient pushes the canister 16 downward, forcing the stem 18 against the element 23, opening the valve mentioned above. In a preferred embodiment of the invention, the interior walls of tube 12 at end 14 and inward may be closely fitted to the walls of canister 16 (a sliding engagement) so the canister 16 will move freely within hollow 20 until stem 18 is stopped by element 23, but is sufficiently close fitting to avoid escape of aerosol spray through open end 14 during use. The FIG. 2 is a top view of the inhaler 10 as shown in FIG. 1, providing further details. As shown in both FIG. 1 and FIG. 2, the up-turned canister 16 slidingly engaged in the hollow 20 through end 14 is accessible to be pushed down on element 23. When depressed upon element 23, the valve on the canister 16 opens to release a metered dose of the aerosol formulation, through stem 18 and conduit 24 to spray from nozzle 26 towards the open end 22 of the tube 12. One dose is released from aerosol canister 16 each time it is fully depressed upon element 23. Release of pressure on canister 16 returns it to the non-depressed position, charging its valve for a further discharge of a dose when the valve is again activated. As shown in FIG. 3 the valve is concealed within the neck of canister 16, and functions when the stem 18 is pushed interiorly of canister 16; the valve itself is not shown in the FIGS. 1–3 being conventional and within the enclosure of the container 16 itself. As described to this point inhaler 10 is a known device, and can be for example as detailed in the U.S. Pat. No. 3,361,306. The known inhaler is modified as described hereinafter to manufacture the inhaler 10 of the invention. Integral to tube 12 and preferably molded on the exterior of tube 12 in a location visible to the user during use, is a hermetically sealed enclosure 30 for the containment of microelectronic means for indicating the number of doses remaining in the canister 16 after each activation and release of a metered dose. The containment of the microelectronic counter means within a hermetically sealed enclosure 30 permits the user to remove the canister 16 at any time, to wash the tube 12 (inside and out) with water, soaps, disinfectants and antiseptic solutions with no damage to or interference with an ongoing count, as will be described more fully hereinafter. This is important, because sprays of many aerosol formulations leave tacky residues which will entrap dust and dirt particles. Some provide a media for the growth of undesired microorganisms. If the growth of these microorganisms is unchecked, they can serve as a source of infection for the patient, and will often introduce pathogens into the patent's respiratory tract. Referring now to FIG. 4, there is seen diagrammatically an enlarged view in cross-section of an embodiment microelectronic means for counting the doses remaining in canister 16, sealed within the enclosure 30. The FIG. 4 does not show the electrical wiring between component parts, for clarity of the drawing. Hermetically sealed within the enclosure 30 is a power source 32, for example, a long-life battery such as the conventional and known nickel-cadmium or lithium batteries putting out circa 1 to 1.5 volts of electric power. Mounted on a printed circuit board 34 and powered by the power source 32 is an application specific integrated circuit (ASIC) 36 such as a logic array or a microprocessor programmed to process electrical signals from a sensor and trigger a signalling device 38 such as, for example, a tactile alerting device, an audible alarm, a visual indicator 40, for example a light emitting diode (LED) or a liquid crystal display (LCD) to give an alpha-numeric readout. LCD devices controlled by electronic signals from ASIC 36 are well known and may be for example the type described in U.S. Pat. Nos. 4,804,953; 5,227,899; and 5,227,901. The ASIC 36 is a control means and if it is more specifically a microprocessor it includes a suitable central processing unit (CPU) for operating the control functions of ASIC 36, described more fully hereinafter. The ASIC 36 can be a digital integrated circuit serving the control functions hereinafter enumerated, including timing functions, calculations of the number of dose actuations, memory recordings, visual and auditory indicators and reporting data to a printer. Actuating the ASIC 36 is a microswitch 42, at least partially within enclosure 30 and mounted for closed, indirect access to the hollow 20 through aperture 44. The term "indirect access" as used herein means that exposure of microswitch 42 to the hollow 20 is shielded by a barrier 46 to be described more fully hereinafter. The nature of barrier 46 is such as to complete the hermetic sealing of enclosure 30, i.e.; it is substantially air and moisture-proof. An optional random access memory (RAM) and/or programmed read only memory (PROM) means 48 is electrically connected to the ASIC 36. The memory means 48 is associated with the ASIC 36 so that a history of the number of actuations remaining can be maintained, together with, for example the date and time of use, for analysis later by the patient's physician in evaluating the patient's condition. The RAM and/or PROM means 48 can be a bubble memory, hysteresis memory or any known memory device. The hermetic sealing of the electronic components within enclosure 30 can be further protected by overcoating the entire assembled circuit within enclosure 30 with a waterproof resin, such as, for example, a polyimide resin or a parylene resin.

Figure 5:
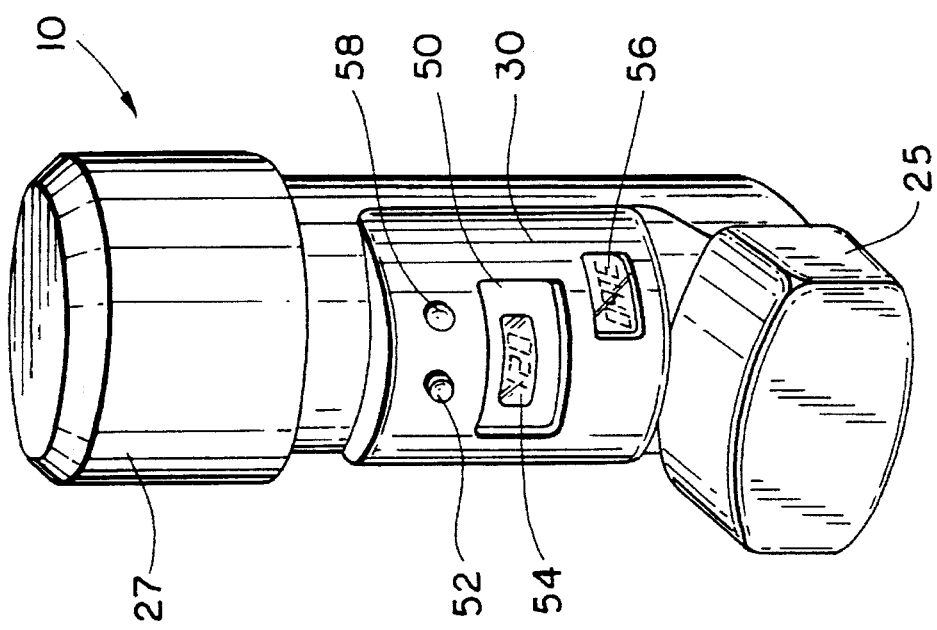
FIG. 5 is a front view of the inhaler of FIG. 1 and the instrumentation panel on the microelectronic means shown in FIG. 4.

FIG. 5 is a front view in perspective of the inhaler 10, including enclosure 30 and showing an example of a preferred instrument panel 50 for use of the microelectronic means employed in the invention. As shown, the instrument panel 50 can include a LED 52 to give visual warning when the aerosol canister 16 is nearing empty. A LED 52 can also give warning when battery life is approaching an end, activated by low threshold voltage in the battery. The LCD 54 can visually give an alpha-numeric reading of the number of doses remaining and optionally other data such as a display 56 of a date and time of last use, battery condition, alarm signals and other data information. As also shown in FIG. 5, the inhaler 10 can also include optionally, a removable cover 25 for the oral mouthpiece at end 22 and a removable cover 27 for frictional fit on the bottom of canister 16 to aid in closing the hollow 20. When the cover 27 is depressed firing the canister 16, the microswitch 42 is closed as described more fully below. An example of the electrical circuitry suitable for the operation of the above described microelectronic means is set forth in the FIG. 6.

The ASIC 36 may be programmed by the manufacturer, to sense and countdown the predetermined number of doses remaining in canister 16 after each use of the assembled apparatus. It can, for example, be programmed to operate as follows:

When a full canister 16 is put into the inhaler 10, depressed and held down for 6 seconds (or any predetermined period for which the unit is programmed), the microelectronic means will reset the electronic counter to 0 and start the count process. This may register on an LCD 54 as, for example, "200" to give a visual count of doses held in the canister 16. While the canister 16 is held down, an audible tone from signalling device 38 may continue for and stop after a predetermined period, for example 6 seconds, to signal that the reset is complete. Alternatively, the ASIC 36 may be programmed to flash the LED in place of an audible tone. During normal usage, the canister 16 may be removed at any time for washing the inhaler 10 and then replaced without altering the ongoing count. After a pre-determined number of resets, for example 12, the LED 52 can be activated to flash continuously to indicate that battery life is nearing termination and that the whole unit of inhaler 10 should be replaced (rather than changing the battery). In view of a battery life indicator, the inhaler 10 is advantageously disposable after use with 12 canisters (or any other number determined by battery size). The dose counter microelectronic means audibly or visually signals after 180 of 200 doses (or any set number) have been dispensed. A red LED 52 may be programmed to flash twice a second for 10 seconds on each use after 180 doses have been administered. After a further 10 doses are dispensed, for instance at dose 191, an audible tone may sound a number of times after each inhaler 10 use indicating the count of remaining doses, upon reaching the final dose, there can be a long sustained audible tone or constant illumination of LED 52 of perhaps 10 seconds duration.

The microelectronic circuit is preferably attached to, or an integral part of, the inhaler 10 at a location on the tube 12. The instrument panel 50 is advantageously visible during use, to the user (patient). Inhaler 10 can accommodate canisters 16 of any volume capacity, for example, 150, 180 or 200 dose units, etc. With a typical 200 dose Albuterol® canister for use by asthmatics, the inhaler 10 of FIGS. 1–3 may function as follows:

The Application Specific integrated Circuit (ASIC) 36 is set at manufacture for a total count of 200 doses. Each time the patient depresses the medication canister 16 for an inhaled dose of Albuterol®, an internal or external microswitch 42 is closed by the downward motion of the canister 16. The microswitch 42 closure triggers the microelectronic means to subtract "one" from any visual indicia count shown by LED 54 and/or flash the LCD 52 one time for about 0.5 seconds. This visual confirmation of count also lets the patient know that there is no battery failure and adequate medication remains for a signalled number of remaining doses. Successive uses to the, for example, 180th dose are confirmed in the same way. Starting with the 181st dose delivery, the LED 52 flashes several times after depressing the canister (perhaps 20 flashes in 10 seconds). This visual signal indicates it is time to seek a refill of the prescribed medication. The signal with each successive dose, repeats to the final dose remaining, (200th), at which time the LED 52 may be programmed to stay on until the battery exhausts or the canister 16 is replaced.

Alternatively, the ASIC 36 can be programmed so that in order for the inhaler 10 to be reusable, the count must be reset when each new canister 16 is introduced. In this version, reset to indicate the number of doses held by a fresh canister 16 may be accomplished by inserting and depressing the new canister 16 for a period of time, for example 5 to 6 seconds. The LED 52 will turn off indicating the reset is complete and the countdown function will start over with the next administered dose. Also, in this alternative at the 200th dose rather than the LED 52 remaining on until the battery fails, an extended blinking period, say 20 seconds, with subsequent shut off may be desirable. One further addition can be an audible alarm which signals the end of useful canister 16 life. We anticipate that the reusable inhaler 10 powered by a conventional lithium battery can be used for about 12 canisters 16. After the 12th canister 16, the inhaler 10 unit would signal the need for replacement by having the LED 52 remain on.

As a further alternative, in conjunction with an LCD 54, the ASIC 36 can be programmed to provide a liquid crystal display (LCD) giving time and date since last dose, number of doses in the past 24 hours and total number of doses remaining. Here too, reset means can be by holding the canister 16 fully depressed for 5 or 6 seconds (or any other predetermined amount of time). The memory means 48 can of course continue to retain previous information (prior to reset) for later evaluation by the patient's physician.

Those skilled in the art will appreciate that an important aspect of the present invention requires a particular trigger to actuate the microelectronic means of countdown. There are several embodiment triggers which will actuate the countdown. In a preferred embodiment inhaler 10 of the invention, the microswitch 42 is a membrane type of electrical switch, such as the well known dome or so-called "bubble" type of electrical contact switch. In this embodiment of FIG. 1, the barrier 46 is a resilient, waterproof barrier sealing the orifice 44, but inwardly movable to close the dome microswitch 42. Pressure from contact with the downward sliding canister 16 in hollow 20 as it passes over the barrier 46 serves to close the microswitch 42 and thereby message a "count" to the ASIC 36.

Alternatively, the microswitch 42 can be a pneumatic pressure responsive switch, the barrier 46 again being of a resilient, waterproof material. Inhalation through end 22 of tube 12 by a patient reduces the ambient pressure in hollow 20. The reduced pressure (vacuum) is sensed by a pressure transducer type of switch 42, sending the message of use for a count to the ASIC 36.

Another microswitch 42 can be of the type responsive to electromagnetic radiation, including reflected light. For example, microswitch 42 may be a light sensor, such as, for example, a LITROXIX BPX-65 sensor connected through the memory means 48 to ASIC 36, and capable of reading the universal product code (UPC) generally imprinted on the canister 16 by the manufacturer. In this case, barrier 46 is light transparent and a source of light such as a red LED in conjunction with the light sensor compresses the microswitch 42 when the UPC code is recognized by memory means 48. UPC readers are well known in the art, and can be, for example, one such as described in U.S. Pat. No. 4,443,694. In this embodiment, when canister 16 is depressed, to align the imprinted UPC with the light sensor, the microprocessor 36 is messaged by recognition in the memory means 48 to effect a countdown.

Alternatively microswitch 42 could be, for example, a proximity switch or an optical sensor to monitor a sight line focused on a spot or pattern imprinted on an inner wall of tube 12 and triggered by obstruction of the spot or pattern from the downward moving canister 16.

Alternatively, a sleeve 17 can be fitted on the canister 16 to slide with canister 16 into the hollow 20 as shown in FIG. 1 (as an option). The leading edge 19 of the sleeve 17 can function to trip the microswitch 42 within the hollow 20, by any of the aforementioned means, replacing contact with the canister 16.

Furthermore, the microswitch 42 can also be located outside of hollow 20, for example, on the exterior of tube 12, as will be described more fully below.

Figure 7:
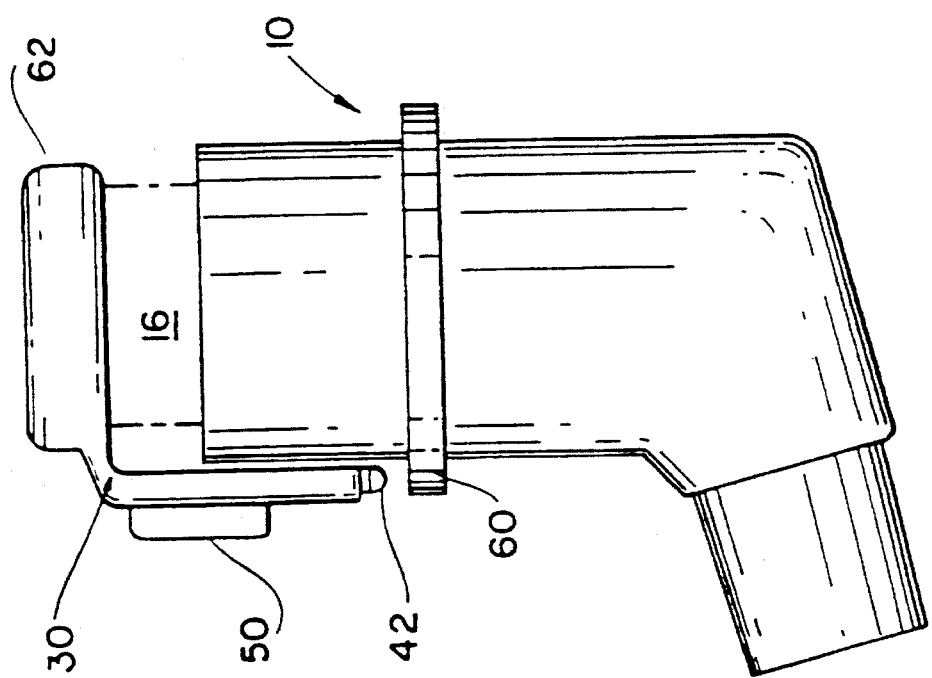
FIG. 7 is a side view-in-perspective of the exterior of another embodiment inhaler of the invention with another microswitch location to actuate the microelectronic means.

In still another embodiment of the invention, as shown in FIG. 7, a side-view in perspective, the inhaler 10 is a prior art apparatus modified only in that a ring stop 60 is integrally molded on the exterior surface of tube 12, a distance distal to the open end 14. The canister 16, upturned and received in the hollow 20 in the normal fashion is fitted with a snap fitting clasp 62, which firmly holds the enclosure 30 with its contained microelectronic means on the canister 16 as described above. The only difference between the embodiment of FIG. 7 and the embodiments of FIGS. 1–3 are that the enclosure 30 is not a part of the tube 12, but becomes an integrated part of the canister 16. The microswitch 42 is on the leading edge of the enclosure 30 as shown in the FIG. 7. In operation, when the canister 16 is depressed within hollow 20, the barrier enclosed microswitch 42 on the leading edge of enclosure 30 makes contact with stop 60 and is thereby triggered as described above. In this embodiment, a simple dome or membrane switch is preferred as the microswitch 42. The microelectric means of FIG. 7 can be reused a number of times with a plurality of canisters 16, and can also be used by retrofitting on existing and known inhalers. The modification comprises simple attachment of a stop 60 to the tube 12 by adhesive or other conventional means, at a point which will make contact with the microswitch 42 when the enclosure 30 carried on canister 16 is moved downward.

In a preferred embodiment inhaler 10 of the invention, the microswitch 42 is an electromagnetic proximity sensor, such as for example the proximity sensor described in U.S. Pat. No. 5,227,764. Referring to FIG. 10, a cross-sectional view of a portion of an inhaler 10" is shown wherein components analogous to those found in the inhaler 10 of FIG. 1 are similarly numbered, but with double prime marks. The inhaler 10" differs essentially from the inhaler 10 in that the microswitch 42 is an electromagnetic proximity sensor 42" enclosed within the enclosure 32" and mounted on the printed circuit board 34". There need be no aperture through the wall of tube 12" into the hollow 20". The sensor 42" will sense a disruption in the electromagnetic field generated by an oscillator. The disruption may be caused by movement of the canister 16" or in the case of the embodiment of FIG. 8 by movement of the diaphragm 68. In either case, the sensor signals a count to the ASIC 36" which then functions as previously described. The proximity switch 42" preferably consists of a capacitor on the printed circuit board 34" which is part of a comparator circuit. When the canister 16" is depressed to the discharge position the comparator detects the movement due to a change in capacitive coupling. The extremely low energy required by the capacitor circuit presents neither power consumption or radio frequency (rf) concerns. Since operational frequency span can be well defined, false triggering by keys or change in one's pocket or purse near the inhaler 10" does not pose a problem. The preferred proximity switch 42" as shown in FIG. 10 and in the circuit of FIG. 12 consists of two capacitors, 200 and 202 the outputs, of which go to a comparator (not shown). The comparator is designed to generate a logic output indicating which is the larger capacitance. One capacitor, 200 the reference, has a fixed value. A second capacitor, 202 the sensing capacitor, could be traces on the circuit board, two copper trails approximately 0.1" wide×0.25" long with 0.05 spacing. All of the circuit board 34 including the capacitor 202, is covered with an insulating parylene resin coating. As long as the sensor capacitance 202 is lower than the reference capacitor 200, the output of the comparator to which they are connected is low. When the drug canister 16" carrying capacitor 200 comes close to the sensing capacitor 202, capacitance increases and comparator output shifts high providing the signal for a count function. An alternative proximity switch uses coils instead of capacitors and measures changes in inductance as the canister 16" comes into proximity with the sensing coil.

The embodiments of FIG. 10 may be fabricated by retrofitting a conventional inhaler of the prior art by attachment of the enclosure 30".

Attachment of enclosure 30" requires no modification of the tube 12". A plastic enclosure 30" is secured on tube 12" by ultrasonic or solvent bonding.

Many modifications of the above described preferred embodiments of inhaler 10 and 10" may be made without departing from the spirit and the scope of the invention. For example, a memory means 48 can be utilized to record the number and dates of use of the inhaler 10 or 10" for subsequent downloading into a written record. Through an input/output unit conventional printer the record can be printed and reviewed by the patient's physician. To facilitate downloading to a printer, the terminal 58 on the instrument panel 50 (see FIG. 5) can facilitate a connection to transmit signals from the memory 48.

EMBODIMENT B

Figure 8:
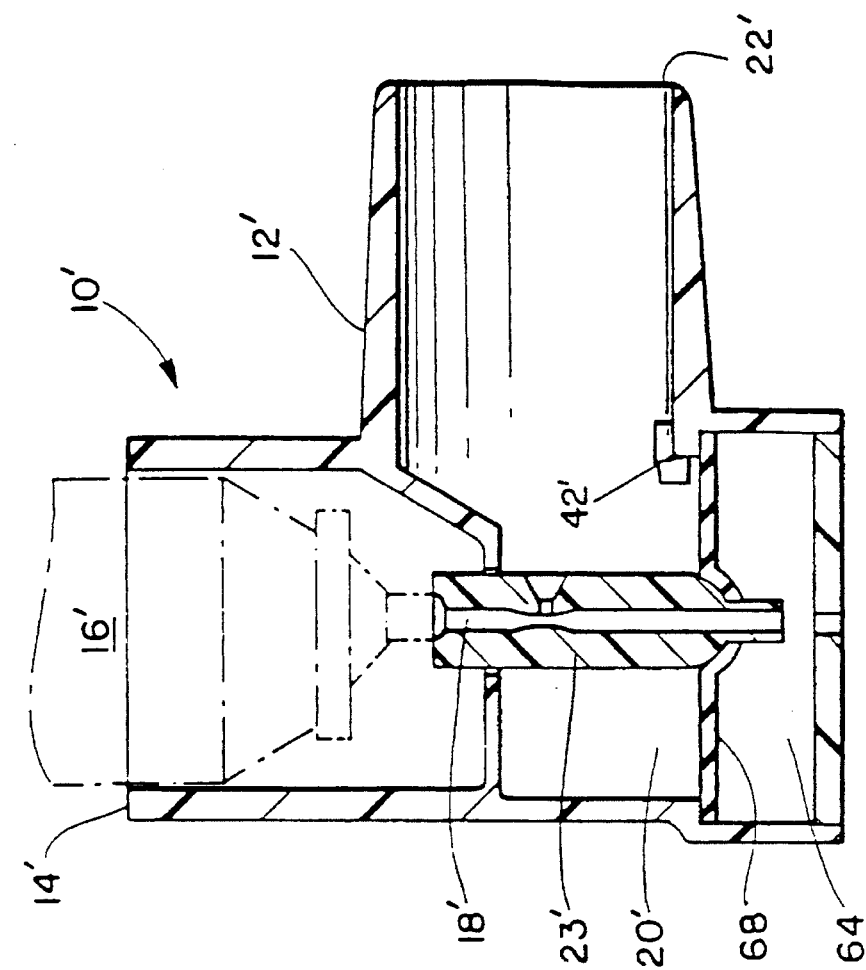
FIG. 8 is a cross-sectional side elevation of an alternate embodiment inhaler of the invention.

As appreciated by those skilled in the art, prior art inhalers are also known which hold the canister 16 in an immobile position, the valve being actuated by movement of the stem 18 inward and outward of the canister 16. Representative of U.S. Patents describing such inhalers are U.S. Pat. Nos. 3,565,070; 4,803,978; 4,955,371; 5,060,643 and the like. This type of inhaler is illustrated in FIG. 8, a cross-sectional side view of an inhaler 10'. In FIG. 8, component parts analogous to those shown in the inhaler 10 of FIGS. 1–3 are numbered with corresponding numbers, followed with a prime mark; i.e.; 10'. As can be seen in FIG. 8, the inhaler 10' differs from the inhaler 10 previously described in that canister 16' is held in a stationary position within the hollow 20' of tube 12'. An air chamber 64 is partitioned from hollow 20' by a flexible diaphragm 68 upon which the element 23' is centered and affixed. In this manner, the canister 16' is held in a fixed position while element 23' is movable in respect to stem 18' so that in response to movement upward or downward by the diaphragm 68 element 23' moves stem 18' inward and outward of the canister 16' for release of a metered dose of the formulation contained in the aerosol canister 16'. The diaphragm 68 is the actuating trigger, moved upward by the vacuum created in hollow 20' when a patient inhales orally upon the mouthpiece at end 22'. Upon cessation of inhalation, the pressure in hollow 20' matches the air pressure in chambers 64 and the diaphragm 68 returns to the lower position (second or normal position) withdrawing the stem 18' and placing the valve in a charged condition for release of the next dose to be administered. In this embodiment, the microswitch 42' is closed by movement of the diaphragm 68 upward into the hollow 20'.

EMBODIMENT C

Figure 9:
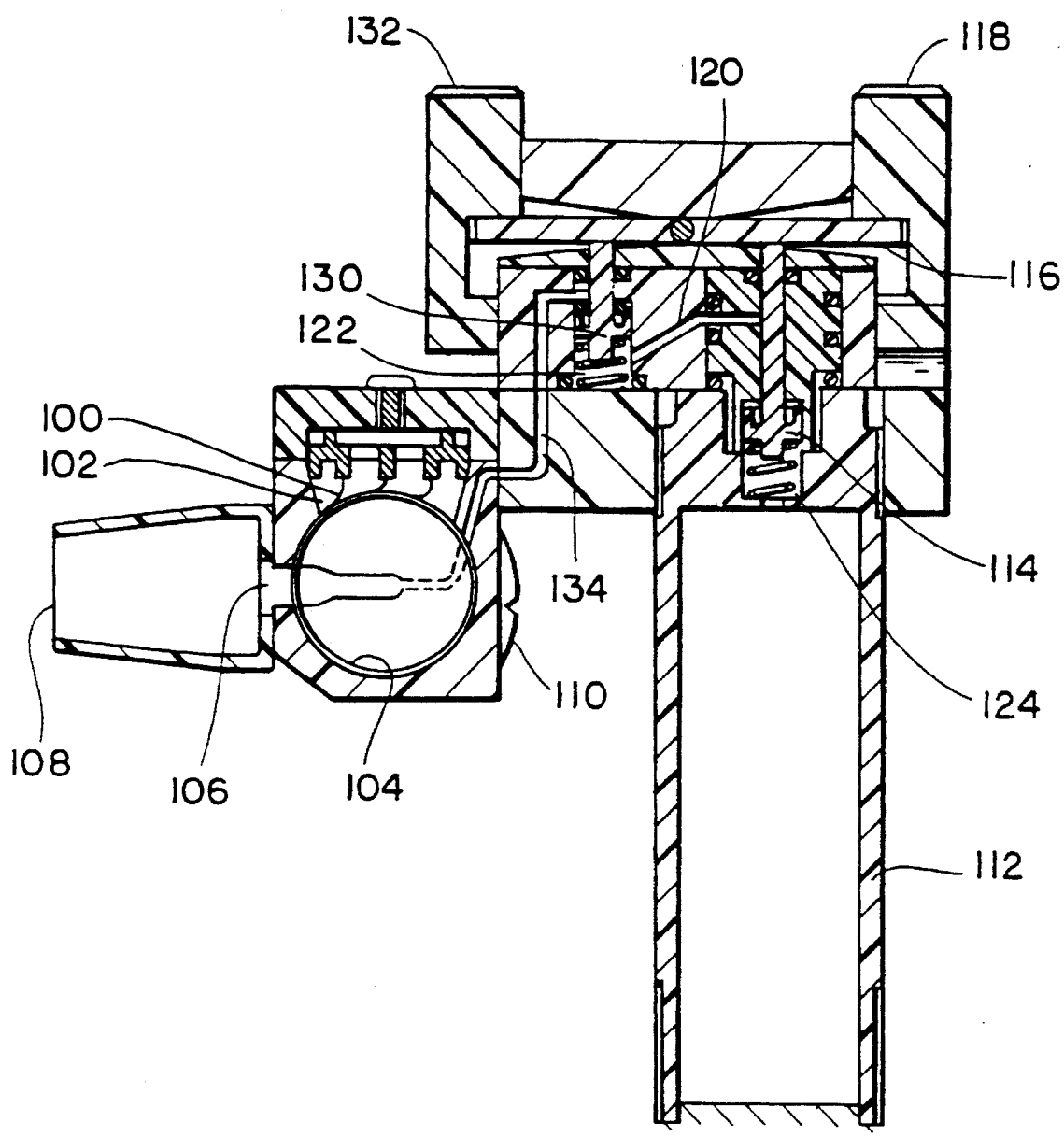
FIG. 9 is still another cross-sectional side elevation of another embodiment inhaler of the invention.
Figure 12:
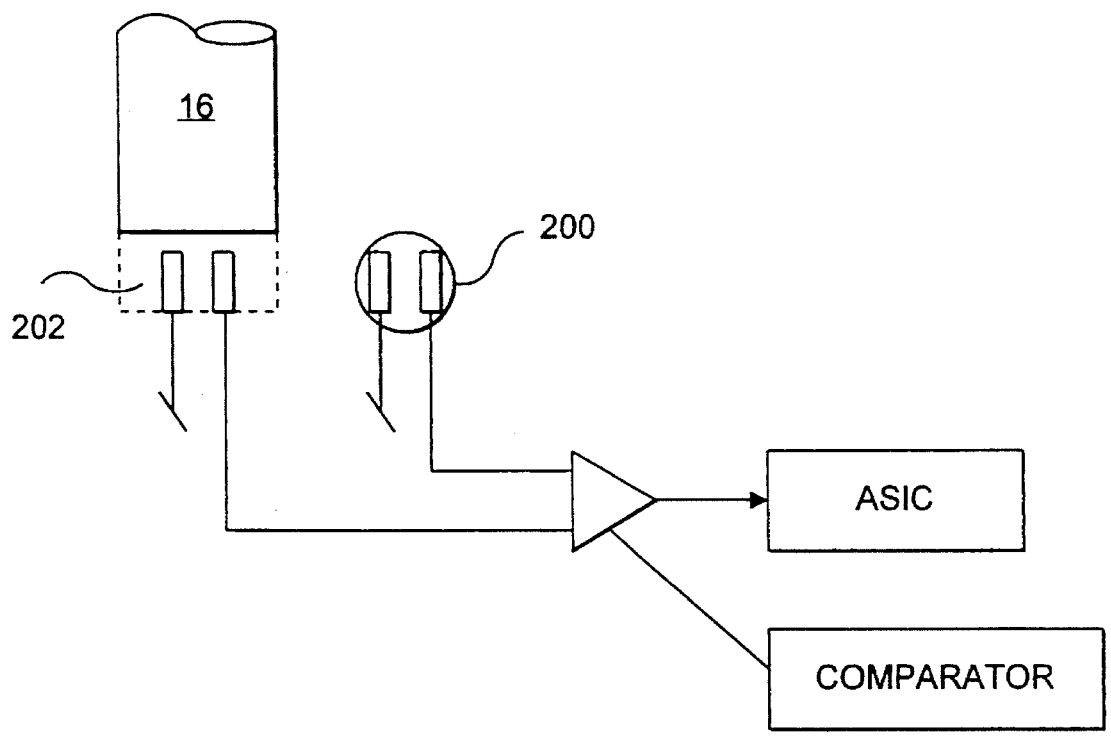
FIG. 12 is a schematic diagram of a preferred circuit for a proximity switch used in the apparatus of the invention.
Figure 13:
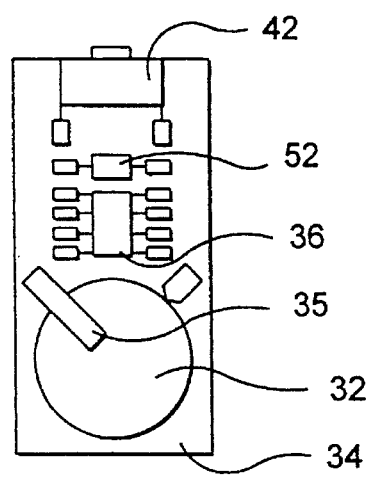
FIG. 13 is a circuit diagram schematically showing a preferred dose counter for use in the invention.
Figure 14:
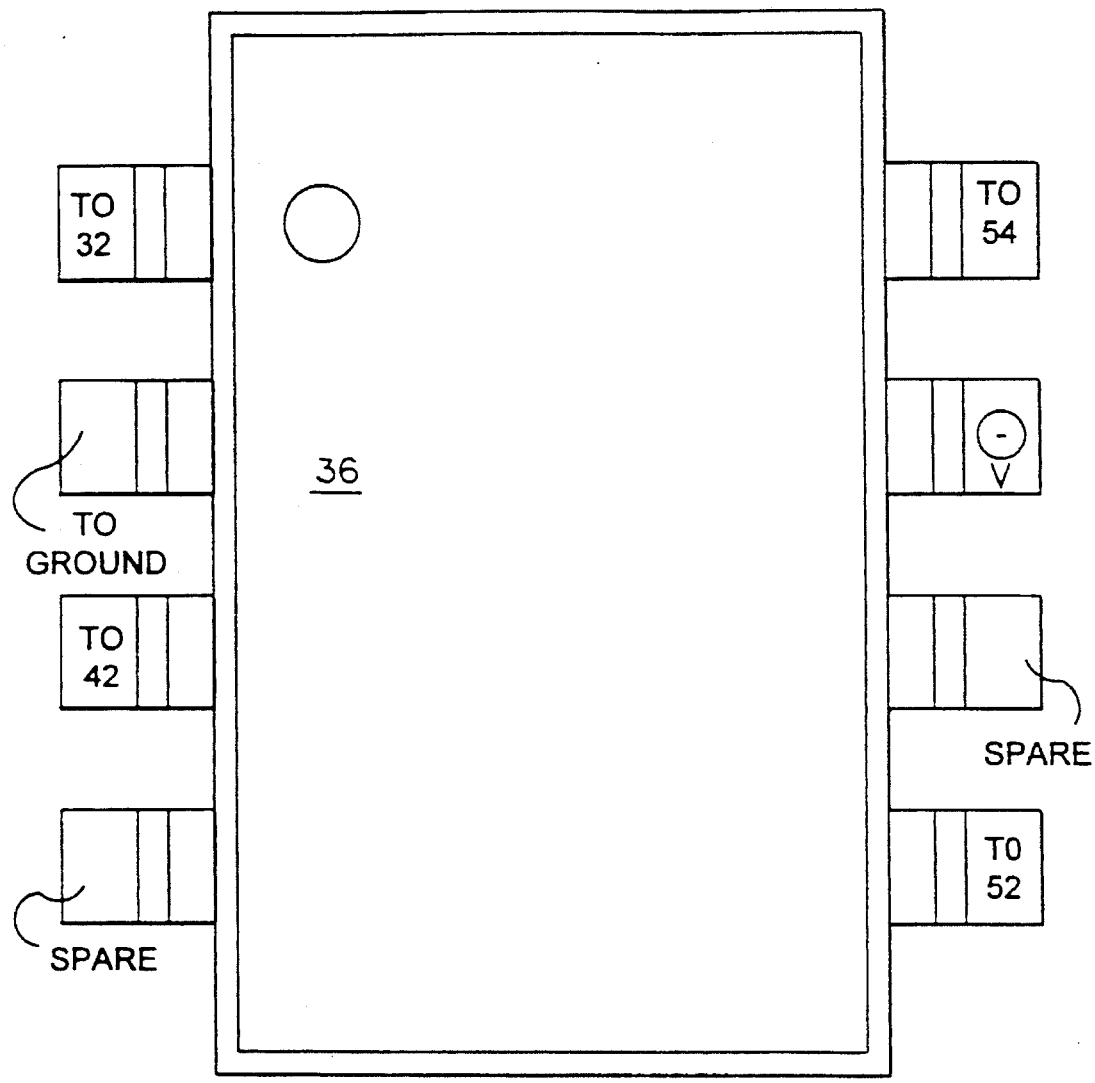
FIG. 14 is a block diagram showing the preferred microelectronic means used in the invention.

Metered dose inhalers are also known in which a solid medication can be delivered in a solution mixed therein from a contained solid form of the medication. Optionally, the solid pharmaceutical can be administered in solid, micronized form; see for example the inhalers described in the U.S. Pat. Nos. 4,524,769; 4,534,345; 4,667,668; 4,668,218; 4,805,811 and 5,337,740. In general, these inhalers function to administer the medication through use of the air flow generated by the patient's oral inhalation (U.S. Pat. No. 4,524,769) or with a propelling, pressurized gas, such as for example, the inhaler of the U.S. Pat. No. 4,667,668, FIG. 1. A quantity of solid medication may be charged to the inhaler of the U.S. Pat. No. 4,667,668, FIG. 1, as shown in the accompanying drawing of FIG. 9. As shown in FIG. 9, the medication 100 is charged to a holding chamber 102 and feeds a rotating membrane 104. When rotated, the membrane 104 receives a quantity of the solid medicament and carries it to a position 106 where it can be discharged to the opening 108 for oral inhalation. A thumb-wheel 110 enables the operator to rotate the membrane 104 for presentation of each dose of medicament to position 106. The medicament 100 is carried from the position 106 to the opening 108 by a stream of propellant from canister 112, upon activation of the inhaler as follows. The valve 114 is opened to release propellant from canister 112 by depression of the portion of tilting lever 116 by pressing trigger 118. With the valve 114 open, liquid or gaseous propellant passes by conduit 120 to dosing chamber 122. When the chamber 120 is filled with propellant, pressure on the tilting lever 116 above the valve 114 ceases, valve 114 closes and the spring 124 in valve 114 assists in closure. Now valve 130 is opened by depressing the trigger 132 upon that portion of tilting lever 116, whereupon the propellant in chamber 122 and conduit 120 is released via conduit 134 to position 106, carrying the dose of medication out of the rotatable membrane 104. The microelectronic means of the present invention can be advantageously connected to the rotation of the thumb-wheel 110 to function with a countdown each time a dose of medication is carried to position 106. The microswitch 42 is advantageously a simple dome type of switch as described above.

Where U.S. patents are referred to above, the contents of their disclosures are thereby incorporated herein by the reference thereto.

Those skilled in the art will appreciate that the invention is broad in scope, and many modifications can be made to the preferred embodiments described above without departing from the spirit and the scope of the invention. For example, as shown in FIG. 11, a view-in-perspective of a further embodiment inhaler of the invention, it can be seen that the tube 12 of the invention can be completely enclosed by having the ends 14, 22 covered by respective covers 27, 25 (the latter being hinged 208 to the exterior of the tube 12. An LCD 54 is positioned on a rear surface of an enclosure 30 which is completely integrated with tube 12 in order to contain the microelectronics. Within the hollow (not seen in FIG. 12) of the tube 12 is positioned a solid or aerosol formulation as described for the embodiments A-C above. Access to the formulations is by removal of the cover 27.

Further, although the preferred embodiments of the invention have been described above as employing sophisticated microelectronic means for indicating the number of formulation doses remaining for further administration to the patient, a relatively simple embodiment includes employment for the microelectronics of a relatively simple count register or "event counter", which will function as a dose administration counter. As diagrammed in the illustration of FIG. 13, the event counter can include a battery 32 mounted on a circuit board 34 with an ASIC 36 and an LED 52 and a momentary microswitch 42, for example a Panasonic EVQQEDO4K. A "Z" clip 35 completes the circuitry. As shown in the FIG. 13, the entire microelectronic circuit can be in size 12.5 mm×25 mm. In this circuit, the ASIC 36 is advantageously as shown in the block diagram of FIG. 14. Such an ASIC 36 may be programmed to include the following functions:

1. LED 52 flashes once for one second with each actuating of the momentary switch to a count of 180.
2. With each actuation from 181 to 199, LED 52 flashes 10 times in 5 seconds.
3. At actuation 200 and beyond, LED 52 comes on and stays on for 10 seconds.
4. Count can be reset to zero when LED 52 comes on after 200 switch actuations by depressing the switch and holding it down for 6 seconds. LED 52 goes off then flashes once indicating reset complete. (Reusable unit).
5. As an alternative to #4 above, at the 200th switch actuation, the LED 52 turns on and remains on until the battery is depleted. (Single use unit).

What is claimed is:

1. An assembly with a metered dose inhalation canister containing a pre-determined number of doses of an aerosol formulation, for delivery orally or intra-nasally, which comprises;
   (a) a hollow closed tube having
      (i) a first open end adapted by size and configuration to receive a spray stem of an aerosol inhalation canister;
      (ii) a second open end adapted by size and configuration to couple with an oral or nasal orifice of a mammal;
   (b) a spray-directing element fixedly located within said tube hollow, and having continuous communication with the first open end and the second open end, for directing sprays of the formulation through a portion of the hollow and out of the second open end of said tube, when the inhalation canister is assembled with the apparatus and activated by a user;
   (c) a metered dose inhalation canister slidably mounted in the first open end of the tube for delivery of a metered dose to the spray-directing element;
   (d) microelectronic means associated with the tube for indicating the number of doses remaining in the canister, after each activation; and
   (e) switch means for activating said microelectronic means, said switch means being isolated from exposure to the tube hollow;
   said microelectronic means being enclosed within a hermetically sealed sleeve housing, mountable on the canister and adapted by size and configuration to slide over the tube exterior.

2. The apparatus of claim 1 wherein the switch means comprises a membrane switch.

3. The apparatus of claim 1 wherein the switch means comprises a membrane switch.

4. The apparatus of claim 1 wherein the switch means comprises a pneumatic pressure responsive switch.

5. The apparatus of claim 1 wherein the switch means comprises a switch responsive to electromagnetic radiation.

6. The apparatus of claim 1 wherein the switch comprises a light sensor.

7. The apparatus of claim 1 wherein the switch comprises a proximity switch.

8. The apparatus of claim 1 wherein the microelectronic means comprises an application specific integrated circuit programmed to indicate the number of doses remaining after each actuation.

9. The apparatus of claim 1 wherein the sleeve has a leading edge which includes the switch means and the tube exterior includes a stop ring for contacting and closing the switch means.

10. The apparatus of claim 1 wherein the microelectronic means includes
    (a) a power source;
    (b) an application specific integrated circuit; and
    (c) a light-emitting diode.

\* \* \* \* \*

UNITED STATES PATENT AND TRADEMARK OFFICE
CERTIFICATE OF CORRECTION

PATENT NO. : 5,544,647
DATED : August 13, 1996
INVENTOR(S) : Warren Jewett and Frederick A. Ebeling It is certified that error appears in the above-indentified patent and that said Letters Patent is hereby corrected as shown below:

Title page, item [54], the title of the patent should read

-- METERED DOSE INHALER -- .

Col. 1, line 1; change "METERED DOSE INHALATOR" to read

-- METERED DOSE INHALER -- .

Signed and Sealed this

Eleventh Day of February, 1997

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,544,647
DATED : August 13, 1996
INVENTOR(S) : Warren Jewett and Frederick A. Ebeling It is certified that error appears in the above-indentified patent and that said Letters Patent is hereby corrected as shown below:

Col. 12, in the claims; Cancel claim 3, which is a duplicate of Claim 2.

Signed and Sealed this

Third Day of March, 1998

Attest:

BRUCE LEHMAN

*Attesting Officer*  *Commissioner of Patents and Trademarks*